United States Patent [19]

Mallik et al.

[11] Patent Number: 4,741,898

[45] Date of Patent: May 3, 1988

[54] STABILIZED STAIN COMPOSITION

[75] Inventors: Arjun Mallik, Pequannock; Daniel Koetters, Butler; Ludmilla Pluto, Pequannock, all of N.J.

[73] Assignee: Fisher Scientific Company, Pittsburgh, Pa.

[21] Appl. No.: 718,308

[22] Filed: Apr. 1, 1985

[51] Int. Cl.$^4$ .......................... G01N 1/00; G01N 1/30; C09B 44/00
[52] U.S. Cl. ............................................. 424/3; 8/506
[58] Field of Search .................... 424/3, 11; 514/2; 8/506

[56] References Cited

U.S. PATENT DOCUMENTS

| | | | |
|---|---|---|---|
| 4,290,769 | 9/1981 | Liao et al. | 8/602 |
| 4,382,075 | 5/1983 | Liao et al. | 424/3 |
| 4,392,864 | 7/1983 | Helfrich et al. | 424/3 |

OTHER PUBLICATIONS

Gilliland, John W., Dean, William W., Stastny, Milos and Lubrano, G. J., Stabilized Romanowsky Blood Stain, *Stain Techn.*, 54(3) 141-150 (1979).

Mahler, Henry R., and Cordes, Eugene H., Biological Chemistry (Harper and Row, New York & London) 1966, pp. 10-14, 190-194.

*Primary Examiner*—Albert T. Meyers
*Assistant Examiner*—Michael S. Wysor
*Attorney, Agent, or Firm*—Alan M. Doernberg

[57] ABSTRACT

Formulations of a cationic dye component (e.g., Azure A-Azure B-Azure C mixtures), an anionic dye component (e.g., Eosin Y) and an alcohol solvent (e.g., methanol or methanol-glycerol mixtures) are stabilized by an amino acid or its acid addition salt (e.g. lysine hydrochloride or glycine or a mixture of these).

12 Claims, No Drawings

STABILIZED STAIN COMPOSITION

BACKGROUND OF THE INVENTION

The present invention relates to compositions for staining biological tissue of the type comprising a cationic dye component, an anionic dye component, a stabilizer and an alcohol-containing solvent; and especially to such compositions of the Romanowsky type.

Romanowsky-type stains, and especially Wright stains, provided in an alcohol solution, are commonly used to stain biological tissue such as blood smears, malarial parasites and bone marrow. Unstabilized compositions are prone to reactions during storage that produce an undesired precipitate and loss of staining ability. A number of proposals have been made regarding the mechanism of this reaction and compositions have been prepared which are stabilized in various ways to counteract these problems. Some of the proposals have involved pH control (Gilliland et. al. *Stain Technology* Vol. 54, No. 3, pp. 141-150 (1979)), introduction of the anionic dye component (especially Eosin Y) in the free acid form rather than the alkali metal salt form (U.S. Pat. No. 4,392,864 to Helfrich et al (1983)) or addition of stabilizers (U.S. Pat. Nos. 4,290,769 (1981) and 4,382,075 (1983), each to Liao et al).

Among the stabilizers proposed have been ammonium halides and primary, secondary or tertiary alkylamine hydrohalides having alkyl chains of 1-6 carbons. Especially mentioned have been diethylamine hydrochloride and dimethylamine hydrochloride; both of which are secondary amines of petrochemical origin.

BRIEF DESCRIPTION OF THE INVENTION

It has been found that amino acids and their acid addition salts, and especially alpha amino acids and their acid addition salts, are effective stabilizers of alcoholic solutions of Romanowsky type stains. Accordingly, the present invention provides a stabilized stain composition comprising:
(a) a cationic dye component,
(b) an anionic dye component,
(c) an alcohol solvent, and
(d) a stabilizer selected from the group consisting of amino acids, substituted amino acids and acid addition salts of amino acids. The prevent invention further provides a method of staining biological tissue which comprises applying to the tissue a stored composition comprising above elements (a), (b), (c), and (d).

DETAILED DESCRIPTION OF THE INVENTION

The present composition contains as essential ingredients two dye components, a solvent and a stabilizer.

A first component in the composition of the present invention is a cationic dye component of the type used in various classes of biological stains. Preferred are the various thiazine components caused by the oxidative demethylation of Methylene Blue:

| Methylene Blue | $+3/2O_2 \rightarrow CO_2 - H_2O$ |
| ↓ | |
| Azure B | $+3/2O_2 \rightarrow CO_2 - H_2O$ |
| ↓ | |
| Azure A | $+3/2O_2 \rightarrow CO_2 - H_2O$ |
| ↓ | |
| Azure C | $+3/2O_2 \rightarrow CO_2 - H_2O$ |
| ↓ | |
| Thionin | |

While the above reactions show the primary products wherein methyl is oxidized completely to $CO_2$ in each instance, partial oxidation to $CH_2O$, $CH_3OH$ and $HCOOH$ may also occur.

One typically uses either the crude mixture of all five components or purified Azure A; nevertheless other combinations or partially purified cuts may be used. Furthermore, other cationic dye components of the type found in biological stains may be used: oxazines Methylene Green, Methylene Violet, Toluidine Blue O and the like.

The anionic dye component of the composition is generally a fluroescein derivative or fluroescein itself; with the preferred anionic dye component being tetra-bromo-fluorescein (commonly called Eosin Y). Such cationic dye components may be used in acid or salt forms (such as the common sodium salt form of Eosin Y).

The concentrations and proportions of the dye components are not independently critical, but it is generally desirable to approximate the stoichiometry that will be followed on staining (e.g. 2:1 mole ratio of thiazine to eosin in most Romanowsky-type stain compositions). Departures from stoichiometry by either component of up to 50% in molar excess are contemplated, however. Wright Stain, for example, is an approximately 1:1:1 mixture (by moles) of Methylene Blue, Azure B and Eosin Y. Solubility limits are normally approached as to the total concentration of anionic and cationic dye components.

The solvent used is an alcohol or alcohol mixture, generally of six carbons or less. For obtaining rapid evaporation, the major alcohol component is preferably methanol, ethanol, or isopropanol, and is most preferably methanol. Glycerol or other diols or triols or sorbitols may also be present to improve stability somewhat. For some applications, however, the concentration of polyols and especially glycerol is preferably kept below 5% (w/v) and more preferably is kept in the 0.5-1.5% range. For other applications (e.g., Wright-Giesma stains), much higher levels (e.g., 50%) of glycerol or the like are used.

The stabilizer used in the present invention is an amino acid or acid addition salt thereof, used in an effective amount to stabilize the stain composition against undesired precipitate forming during storage, and especially against the progressive formation of such precipitates over a period of a few weeks or less. A preferred class of such stabilizers are the alpha amino acids and acid additions salts thereof because of their relatively innocuous character, being naturally occuring substances in biological materials. Among the amino acids, either D or L forms (or even other stereoisomers such as the meso form) may be used, or mixtures such as racemic mixtures may be used. L-amino acids are preferred. All classes of amino acids (cationic such as lysine or histidine, neutral such as glycine or anionic such as aspartic or glutamic acid) may be used; the aromatic amino acids tryptophan, phenylalanine and tyrosine, may also be used. Most preferred are lysine, glycine, lysine acid addition salts (especially the monoacid addition salts) and glycine acid addition salts. Among the acid addition salts, hydrohalides are preferred and hydrochlorides are more preferred. Esters of amino acids and their acid addition salts may also be used.

While not wishing to be bound to the mechanism by which the present stabilizers work, it is postulated that a trace of aldehyde may form in stain compositions by an oxidation (e.g., of methanol to formaldehyde) and that such trace aldehydes may react with the phenolic and amino dyes to form condensates which precipitate. Amino acids can scavenge the trace aldehydes (forming $CH_2=N-CHR-COOH$ from formaldehyde and alpha amino acid), thus preventing the precipitating condensates.

Stated differently, a preferred class of stain compositions comprise:
(a) a mixture of Azures A, B, and C,
(b) Eosin Y,
(c) methanol, and
(d) an alpha amino acid or acid addition salt of an alpha amino acid (which is more preferably lysine, a lysine acid addition salt, glycine or a glycine acid addition salt).

Such preferred class of stain composition may also contain glycerol. In such composition, components (a) and (b) (in approximately stoichiometric ratios) typically comprise 0.1–1.0% (w/v) of the total composition, component (d) typically comprises 0.0–2.0% (w/v) of the total composition and methanol the balance (except for up to 5% glycerol which may be present in Wright Stain or about 50% glycerol which may be used in Wright-Geisma stain).

EXAMPLES 1-5

Compositions were prepared by mixing the ingredients shown in Table 1. All units are grams, except for methanol and glycerol, which are expressed in milliliters.

TABLE 1

| Formulation: | 1 | 2 | 3 | C4 | 5 |
|---|---|---|---|---|---|
| Ingredients: | | | | | |
| Azure A | 3 | 3 | 3 | 3 | — |
| Eosin Y (Na$_2$) | 3 | 3 | 3 | 3 | — |
| Wright Stain | — | — | — | — | 3 |
| Glycerin | 2 | — | 2 | — | 2 |
| Lysine - HCl | 4 | 4 | — | — | — |
| Diethylamine HCl | — | — | — | 4 | — |
| Methanol | 2000 | 2000 | 2000 | 2000 | 2000 |

Two weeks after formulation, the five compositions were tested on smears of human blood. Ratings (based upon a value of 4.0 for a fresh commercial product) were 3.8 for formulations 2 and 3, 3.7 for formulation 1, 1.5 for formulation 5 and 1.0 for control formulation 4. These results suggest that either lysine HCl or glycerol (but not both together if glycerol is 2%) are highly effective in this type of formulation; and that diethylamine hydrochloride was least effective.

EXAMPLE 6 AND 7

Formulations were then prepared with 1.5 g of Azure A (80% purity), 1.5 g of Eosin Y (85% purity of the disodium salt), 5 g of glycerol, one liter of methanol and 2 g of either lysine hydrochloride (in Example 6) of 2 g of glycine (in Example 7). Portions of each formulation were stored at 25° C. and at 37° C. and were taken periodically and assayed for Eosin Y (absorption at 525 mm), for Azure A (absorption at 640 mm) and staining score.

The lysine-containing formulation (Example 6) showed excellent (over 90%) retention of Eosin Y content up to 150 days at 37° C. (somewhat less at 25° C.), and staining scores that declined only very slowly, being 90% of ideal and 90% of the initial value after 150 days at 25° C. Larger scale batches performed somewhat similarly.

The glycine-containing formulation of Example 7 also showed excellent retention of values for Eosin Y and Azure A based upon absorbance. The staining scores were also quite good through 270 days storage, except that performance began deteriorating badly after 2 months exposure to 2° C. When, however, lysine hydrochloride and glycine were present together in the formulation, staining performance was good even at 2° C. and −10° C.

Compositions have also been prepared containing lysine hydrochloride and glycine and glycerol. All performed well when stored at 25° C., and the glycine-containing formulations performed well when stored and-/or used at lower temperatures (typically 2° C.).

We claim:
1. A stabilized Romanowsky-type stain composition comprising:
   (a) a cationic dye component selected from the group consisting of Methylene Blue, Azure A, Azure B, Azure C, thionin and mixtures thereof,
   (b) an anionic dye component selected from the group consisting of Eosin Y, Eosin B, fluorescein, a substituted fluorescein, Orange G and mixtures thereof,
   (c) an alcohol solvent of 1–6 carbons, and
   (d) an effective amount of a stabilizer selected from the group consisting of lysine, glycine and acid addition salts of lysine and glycine.
2. The stabilized stain composition of claim 1 wherein the anionic dye component is Eosin Y.
3. The stabilized stain composition of claim 2 wherein the stabilizer is glycine or a glycine acid addition salt.
4. The stabilized stain composition of claim 2 wherein the stabilizer is lysine or a lysine acid addition salt.
5. The stabilized stain composition of claim 2 wherein the alcohol solvent comprises methanol.
6. The stabilized stain composition of claim 2 wherein the alcohol solvent comprises methanol and glycerol.
7. The stabilized stain composition of claim 1 wherein the alcohol solvent comprises methanol.
8. The stabilized stain composition of claim 1 wherein the cationic dye component comprises a mixture of Azures A, B, and C.
9. The stabilized stain composition of claim 8 wherein the anionic dye component is Eosin Y and the alcohol solvent is methanol.
10. The stabilized stain composition of claim 9 further comprising glycerol.
11. A method of staining biological tissue which comprises applying to the tissue a stored Romanowsky-type stain composition comprising:
   (a) a cationic dye component selected from the group consisting of Methylene blue, Azure A, Azure B, Azure C, thionin and mixtures thereof,
   (b) an anionic dye component selected from the group consisting of Eosin Y, Eosin B, fluorescein, a substituted fluorescein, Orange G and mixtures thereof,
   (c) an alcohol solvent of 1–6 carbons, and
   (d) an effective amount of a stabilizer selected from the group consisting of lysine, glycine and acid addition salts of lysine and glycine.
12. The method of claim 11 wherein the cationic dye component is a mixture of Azures A, B and C, the anionic dye component is Eosin Y and the alcohol solvent is methanol.

* * * * *